United States Patent
Doyle et al.

(10) Patent No.: US 10,463,758 B2
(45) Date of Patent: Nov. 5, 2019

(54) DEVICE FOR EVAPORATING VOLATILE SUBSTANCES

(71) Applicant: ZOBELE ESPAÑA, SA, Barcelona (ES)

(72) Inventors: Dominic Doyle, Barcelona (ES); Ruben Garcia Fabregas, Barcelona (ES); Sergio Luque Vera, Barcelona (ES)

(73) Assignee: ZOBELE EXPANA, S.A., Barcelona (ES)

( * ) Notice: Subject to any disclaimer, the term of this patent is extended or adjusted under 35 U.S.C. 154(b) by 0 days.

(21) Appl. No.: 15/325,585

(22) PCT Filed: Jul. 10, 2015

(86) PCT No.: PCT/ES2015/070542
§ 371 (c)(1),
(2) Date: Jan. 11, 2017

(87) PCT Pub. No.: WO2016/005647
PCT Pub. Date: Jan. 14, 2016

(65) Prior Publication Data
US 2017/0151360 A1   Jun. 1, 2017

(30) Foreign Application Priority Data
Jul. 11, 2014   (ES) ...................... 1431047

(51) Int. Cl.
*F23N 1/02*   (2006.01)
*A61L 9/03*   (2006.01)
(Continued)

(52) U.S. Cl.
CPC ............... *A61L 9/03* (2013.01); *A01M 1/20* (2013.01); *A61L 9/02* (2013.01); *F23D 3/16* (2013.01); *G01K 7/22* (2013.01); *F23D 2208/10* (2013.01)

(58) Field of Classification Search
CPC ... F23Q 25/00; F23D 3/00; F23D 3/02; F23D 3/16; F23D 3/18
(Continued)

(56) References Cited

U.S. PATENT DOCUMENTS 4,781,895 A   11/1988   Spector
6,354,710 B1   3/2002   Nacouzi
(Continued)

FOREIGN PATENT DOCUMENTS

EP   1321036 A2   6/2003
FR   2294717 A1   7/1976
(Continued)

OTHER PUBLICATIONS

International Search Report for PCT/ES2015/070542, dated Sep. 8, 2015.
(Continued)

*Primary Examiner* — Vivek K Shirsat
(74) *Attorney, Agent, or Firm* — Kutak Rock LLP

(57) ABSTRACT

The invention relates to a device for evaporating volatile substances, comprising a heat source (5) evaporating volatile substances from a refill (2), a heat detector (4) which can detect the heat from said heat source (5), and indicating means (7) connected to said heat detector (4) emitting an indication when the heat detector (4) detects the heat from said heat source (5), and characterized in that said heat detector (4) is placed above said heat source (5).

The invention allows the indicating means to be activated virtually in a simultaneous manner with the placement of the heat emitter.

17 Claims, 1 Drawing Sheet

(51) Int. Cl.
  *A01M 1/20* (2006.01)
  *A61L 9/02* (2006.01)
  *F23D 3/16* (2006.01)
  *G01K 7/22* (2006.01)

(58) Field of Classification Search
  USPC .......................................... 431/288–325, 33
  See application file for complete search history.

(56) References Cited

U.S. PATENT DOCUMENTS

| | | | |
|---|---|---|---|
| 6,491,516 B1 | 12/2002 | Tal et al. | |
| 2002/0119413 A1* | 8/2002 | Cheng | A63J 17/00 431/289 |
| 2006/0024627 A1* | 2/2006 | Platts | F23D 3/16 431/14 |
| 2007/0117059 A1 | 5/2007 | Goldenberg | |
| 2007/0128561 A1* | 6/2007 | Hart | F23D 3/16 431/33 |
| 2009/0200393 A1 | 8/2009 | Avelar | |
| 2011/0045415 A1* | 2/2011 | Shitrit | B44F 1/10 431/2 |

FOREIGN PATENT DOCUMENTS

| | | |
|---|---|---|
| WO | 0078135 A2 | 12/2000 |
| WO | 0319082 A1 | 3/2003 |
| WO | 2007138246 A2 | 12/2007 |
| WO | 2007138246 A3 | 12/2007 |
| WO | 2008132733 A1 | 11/2008 |

OTHER PUBLICATIONS

European Search Report and Written Opinion for PCT/ES2015070542 dated Jan. 23, 2018.

* cited by examiner

DEVICE FOR EVAPORATING VOLATILE SUBSTANCES

This is the United States National Stage of Patent Cooperation Treaty Application No. PCT/ES2015/070542 filed Jul. 10, 2015, which claims priority to Spanish Patent Application No. P201431047 filed Jul. 11, 2014, the disclosures of which are incorporated herein by reference in their entireties.

The present invention relates to a device for evaporating volatile substances comprising a heat emitter evaporating volatile substances contained in a refill.

BACKGROUND OF THE INVENTION

Devices containing candles which, when lit, detect flame and activate a set of lights are well known on the market. Generally, these devices act by means of a light detector and sometimes by means of a heat detector.

Lights in devices of this type allow users to check that the evaporating device is in operation by simply looking at it.

In known evaporating devices, the position of this sensor is below the position of the candle. In defining the mentioned configuration, particularly if they use heat detectors, there is a drawback resulting from the thermal inertia of the system.

These devices work by activating the lights once a specific temperature is reached in the heat detector. This means that the consumer must wait for a few minutes after lighting the candle in order to see how the set of lights lights up.

There is therefore a need for an evaporating device in which the indications are activated almost immediately when a candle is lit.

DESCRIPTION OF THE INVENTION

The evaporating device of the invention solves the mentioned drawbacks, having other advantages that will be described below.

The device for evaporating volatile substances according to the present invention comprises a heat source for evaporating volatile substances from a refill, a heat detector which can detect the heat from said heat source, and indicating means connected to said heat detector emitting an indication when the heat detector detects the heat from said heat source, and it is characterized in that said heat detector is placed above said heat source.

For example, the heat detector is placed at a distance between 5 mm and 20 mm from the heat source.

Advantageously, said heat detector is arranged in a cantilevered portion placed above said heat source.

According to a preferred embodiment, said heat detector is a thermistor, said refill is a candle and said heat source is a flame.

Furthermore, said indicating means preferably comprise at least one light emitter, such as one or more light emitting diodes (LEDs), or a sound emitter, or the like.

Furthermore, said heat detector and said indicating means are advantageously connected to one or more batteries.

According to a preferred embodiment, said heat detector and said indicating means are connected to a microprocessor, such that said indicating means are activated or emit an indication when the microprocessor receives a signal from the heat detector and determines an increase in heat of at least 1° C. per second.

The device for evaporating volatile substances according to the present invention allows the indicating means to be activated virtually in a simultaneous manner with the placement of the heat emitter, i.e., upon lighting the flame of the candle, according to the preferred embodiment. This is achieved as a result of the proximity of the heat detector with respect to said heat emitter.

BRIEF DESCRIPTION OF THE DRAWINGS

To better understand what has been set forth, drawings schematically depicting a practical embodiment only by way of a non-limiting example are attached.

DESCRIPTION OF A PREFERRED EMBODIMENT

Figure 1:
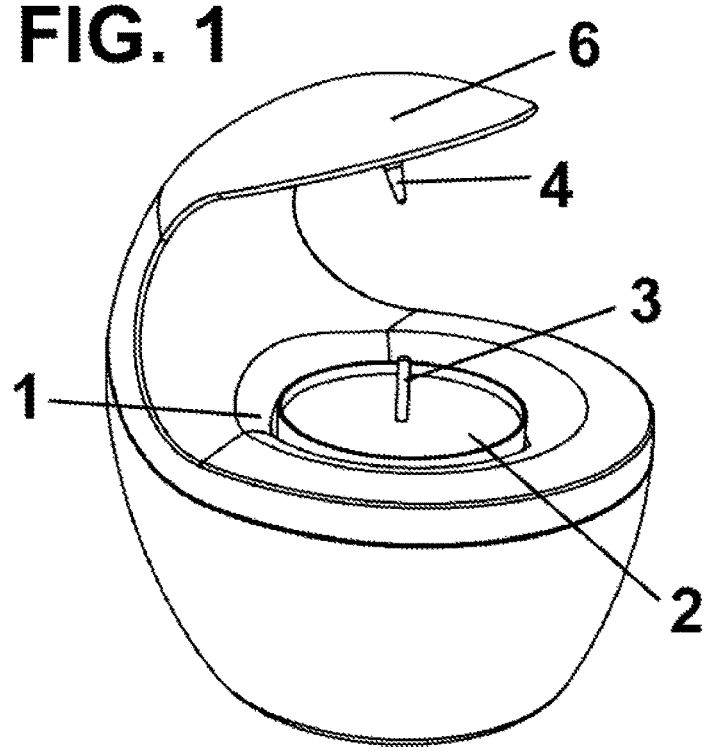
FIG. 1 is a perspective view of the device for evaporating volatile substances according to the present invention.
Figure 2:
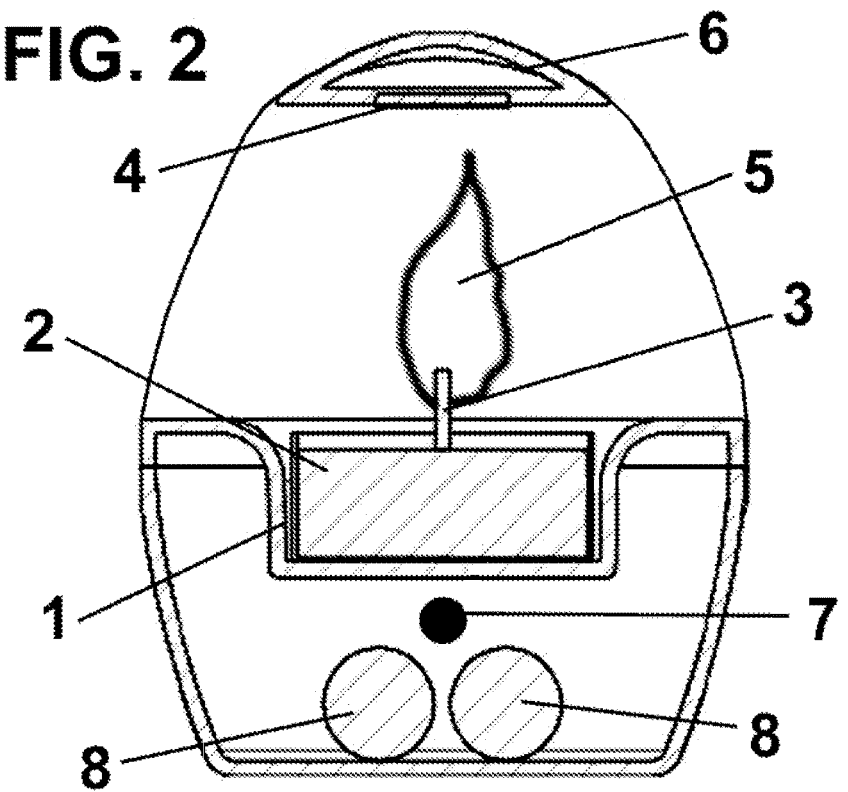
FIG. 2 is an elevational view of the device for evaporating volatile substances according to the present invention sectioned.

The evaporating device according to the present invention comprises a housing 1 for a refill, for example, a candle 2 provided with a wick 3, and a heat detector 4, for example, a thermistor.

This heat detector 4 is located in an elevated position right above a heat source 5, for example, a flame burning from the wick 3 of said candle 2. According to the depicted embodiment, said heat detector 4 is placed in a cantilevered portion 6 of the device, as can be seen in the drawings. This position is suitable to be able to detect heat from the flame.

For example, the heat detector 4 is placed at a distance between 5 mm and 20 mm from the heat source 5.

Furthermore, the evaporating device according to the present invention also comprises indicating means, for example, at least one light emitter 7, such as one or more light emitting diodes (LEDs) emitting light of one or more colors, allowing the user to see whether or not the heat source 5 is active by simply looking at it.

It must be indicated that said indicating means could also be sound emitting means such as a loudspeaker that plays a melody.

According to the depicted embodiment, said heat detector 4 and said LED 7 are connected to a microprocessor (not depicted in the drawings), such that said LED 7 lights up when the microprocessor receives a signal from the heat detector 4 and an increase in heat of at least 1° C. per second is determined.

If the microprocessor determines an increase in temperature less than 1° C. per second, it will then send a signal to the LED 7 for it to shut off.

Preferably, the at least one light emitter 7 is powered by means of one or more batteries 8, although it could also be connected to the electric current or any suitable power source.

Obviously, the material of the device according to the present invention is suitable for withstanding high temperatures and being arranged close to a flame. Furthermore, if desired, it can be a transparent or translucent material.

Although reference has been made to a specific embodiment of the invention, it is obvious for a person skilled in the art that the evaporating device described is susceptible to a number of variations and modifications, and that all the mentioned details can be replaced with other technically equivalent details without departing from the scope of protection defined by the attached claims.

The invention claimed is:

1. Device for evaporating volatile substances comprising a heat source (5) for evaporating volatile substances from a refill (2), a heat detector (4) which can detect the heat from said heat source (5), and indicating means (7) connected to said heat detector (4) emitting an indication when the heat detector (4) detects the heat from said heat source (5), characterized in that said heat detector (4) is mounted on a generally horizontal fixed cantilevered structure (6) such that said heat detector (4) is fixedly positioned above said heat source (5).

2. Device for evaporating volatile substances according to claim 1, wherein the heat source (5) is exposed to the environment.

3. Device for evaporating volatile substances according to claim 1, wherein said heat detector (4) is a thermistor.

4. Device for evaporating volatile substances according to claim 1, wherein said refill is a candle (2) provided with a wick (3) and said heat source is a flame (5).

5. Device for evaporating volatile substances according to claim 1, wherein said indicating means comprise at least one light emitter (7).

6. Device for evaporating volatile substances according to claim 1, wherein said heat detector (4) and said indicating means (7) are connected to one or more batteries (8).

7. Device for evaporating volatile substances according to claim 1, wherein said heat detector (4) and said indicating means (7) are connected to a microprocessor, such that said indicating means (7) are activated when the microprocessor receives a signal from the heat detector (4) and determines an increase in heat of at least 1° C. per second.

8. A device for evaporating volatile substances, the device comprising:
a housing (1) having a first area for receiving a refill (2);
a fixed cantilevered structure (6) extending generally horizontally from the housing (1);
a heat detector (4) mounted on said fixed structure (6); and
an indicating means (7) in communication with the heat detector (4),
wherein the refill (2) comprises a volatile substance,
wherein the volatile substance of the refill (2) evaporates upon being heated by a heat source (5) associated with the refill (2), and
wherein said fixed structure (6) extends over at least a portion of the first area of said housing such that said heat detector (4) is fixedly positioned above the heat source (5) when the refill (2) is received by the first area of said housing (1).

9. The device of claim 8, wherein the fixed cantilevered structure is generally parallel with the first area of the housing.

10. The device of claim 9, wherein the heat detector (4) is positioned at a distal end of the cantilevered structure, the distal end of the cantilevered structure being positioned directly above the heat source when the refill is received by the first area of said housing.

11. The device of claim 10, wherein the heat source (5) is exposed to the environment while the refill (2) is received by the first area of said housing (1).

12. The device of claim 8, wherein the heat source (5) is exposed to the environment while the refill (2) is received by the first area of said housing (1).

13. The device of claim 8, wherein the first area is generally horizontal.

14. The device of claim 8, wherein the housing comprises a generally vertical portion extending between said cantilevered structure and said first area of said housing.

15. The device of claim 1, wherein the refill is configured to rest upon a first area of the device, said fixed cantilevered structure being generally parallel with said first area.

16. The device of claim 1, wherein the refill is configured to rest upon a first area of the device, the first area being generally horizontal.

17. The device of claim 1, wherein the refill is configured to rest upon a first area of the device, the device comprising a generally vertical portion extending between said cantilevered structure and said first area.

* * * * *